US007331994B2

(12) United States Patent
Gordon et al.

(10) Patent No.: US 7,331,994 B2
(45) Date of Patent: *Feb. 19, 2008

(54) INTERVERTEBRAL DISC REPLACEMENT PROSTHESIS

(75) Inventors: Jeffrey D. Gordon, Nashville, TN (US); John K. Song, Chicago, IL (US)

(73) Assignee: Vanderbilt University, Nashville, TN (US)

( * ) Notice: Subject to any disclaimer, the term of this patent is extended or adjusted under 35 U.S.C. 154(b) by 509 days.

This patent is subject to a terminal disclaimer.

(21) Appl. No.: 10/903,578

(22) Filed: Jul. 30, 2004

(65) Prior Publication Data

US 2005/0043804 A1 Feb. 24, 2005

Related U.S. Application Data

(63) Continuation-in-part of application No. 10/235,117, filed on Sep. 5, 2002, now Pat. No. 6,964,686, which is a continuation-in-part of application No. 09/572,057, filed on May 17, 2000, now Pat. No. 6,579,321.

(60) Provisional application No. 60/134,500, filed on May 17, 1999.

(51) Int. Cl.
*A61F 2/44* (2006.01)
(52) U.S. Cl. ............................. 623/17.13; 623/17.16
(58) Field of Classification Search .. 623/17.11–17.16; 606/60, 61
See application file for complete search history.

(56) References Cited

U.S. PATENT DOCUMENTS

| 4,309,777 | A | 1/1982 | Patil |
| 4,932,975 | A | 6/1990 | Main et al. |
| 5,320,644 | A | 6/1994 | Baumgartner |
| 5,415,704 | A | 5/1995 | Davidson |
| 5,423,817 | A | 6/1995 | Lin |
| 5,458,642 | A | 10/1995 | Beer et al. |
| 5,507,816 | A | 4/1996 | Bullivant |

(Continued)

FOREIGN PATENT DOCUMENTS

EP 0 538 183 A1 4/1993

(Continued)

OTHER PUBLICATIONS

Afanas'ev, V.V., "Electronic Properties of $SiO^2$/SiC Interfaces," *Microelectronic Engineering*, No. 48, pp. 241-248 (1999).

(Continued)

*Primary Examiner*—Alvin J. Stewart
(74) *Attorney, Agent, or Firm*—Tim Tingkang Xia, Esq.; Morris, Manning & Martin

(57) ABSTRACT

An intervertebral disc prosthesis for placement between a first vertebra and a second vertebra adjacent to the first vertebra. In one embodiment, the intervertebral disc prosthesis includes a resilient member, a first support member and a second support member. The first support member and the second support member are housed into the resilient member that is arranged, in use, to be secured to the first vertebra and the second vertebra, respectively. The intervertebral disc prosthesis can generate a coupled motion in more than one possible direction responsive to a possible movement of at least one of the first vertebra and the second vertebra, among the resilient member, the first support member and the second support member.

43 Claims, 9 Drawing Sheets

U.S. PATENT DOCUMENTS

| | | | |
|---|---|---|---|
| 5,556,431 | A | 9/1996 | Buttner-Janz |
| 5,676,702 | A | 10/1997 | Ratron |
| 5,782,832 | A * | 7/1998 | Larsen et al. ............... 606/61 |
| 5,827,328 | A | 10/1998 | Butterman |
| 5,865,846 | A * | 2/1999 | Bryan et al. ............... 128/898 |
| 5,888,223 | A | 3/1999 | Bray, Jr. |
| 5,888,226 | A | 3/1999 | Rogozinski |
| 5,895,428 | A | 4/1999 | Berry |
| 6,117,174 | A | 9/2000 | Nolan |
| 6,136,031 | A | 10/2000 | Middleton |
| 6,146,421 | A * | 11/2000 | Gordon et al. ........... 623/17.15 |
| 6,296,664 | B1 * | 10/2001 | Middleton ............... 623/17.15 |
| 6,368,350 | B1 * | 4/2002 | Erickson et al. ......... 623/17.14 |
| 6,395,035 | B2 | 5/2002 | Bresina et al. |
| 6,579,321 | B1 | 6/2003 | Gordon et al. |
| 6,582,468 | B1 * | 6/2003 | Gauchet ................. 623/17.16 |
| 6,964,686 | B2 * | 11/2005 | Gordon .................. 623/17.14 |
| 6,986,789 | B2 * | 1/2006 | Schultz et al. ........... 623/17.15 |
| 7,128,761 | B2 * | 10/2006 | Kuras et al. ............. 623/17.15 |

FOREIGN PATENT DOCUMENTS

| | | |
|---|---|---|
| EP | 538183 A1 | 4/1993 |
| EP | 0 985 384 A1 | 3/2000 |
| FR | 2 734 148 A1 | 5/1995 |
| FR | 2 799 116 A1 | 4/2001 |
| FR | 2799116 A1 * | 4/2001 |

OTHER PUBLICATIONS

Benzel, Edward C., Spine Surgery: Techniques, Complication Avoidance, and Management, ISBN 0-443-07540-9, Sec.11, pp. 149-192 (1999).

Biomechanics—BAK™ Interbody Fusion System brochure; SulzerMedica, Sulzer Spine Tech; (1999).

Enker, P., et al., "Artificial Disc Placement, Preliminary Report with a 3-year Minimum Follow-Up," Spine, vol. 18, No. 8, pp. 1061-1070 (1993).

Hedman, Thomas, et al., "Design of an Intervertebral Disc Prosthesis, Spine Surgery," Spine, vol. 16, No. 6 Supplement, pp. S256-S259 (1990).

"Intervertebral Dynamic Disc Spacer," www.linkspine.com, 3 pages (2002).

Kostuik, John P., "Intervertebral Disc Replacement, Experimental Study," Clinical Orthopedics and Related Research, No. 337, pp. 27-41 (1997).

Lai, P.T. et al., "Effects of Nitridation and Annealing on Interface Properties of Thermally Oxidized $SiO_2$/SiC Metal-Oxide-Semiconductor System," Applied Physics Letters, vol. 76, No. 25, pp. 3744-3746 (2000).

Lee, Casey K., et al., "Development of a Prosthetic Intervertebral Disc" Spine Surgery, vol. 16, No. 6 Supplement, S253-S255 (1991).

Li, Hui-Feng, et al., "Improved Reliability of NO-Nitrided $SiO_2$ Grown on p-Type 4H-SiC," IEEE Electron Device Letters, vol. 19, No. 8, p. 279-281 (1998).

Lipkin, Lori A, et al., "Insulator Investigation on SiC for Improved Reliability," IEEE Transactions on Electron Devices, vol. 46, No. 3, pp. 525-532, (1999).

Manufacturer Directory, ArificialDisc.com, 2 pages (2000).

Patent Guide—BAK™ Interbody Fusion System brochure; SulzerMedica, Sulzer Spine Tech (1999).

"PRODISC®," www.spinesolutions.com 2 pages (2002).

"Ray Threaded Fusion Cage™ A Better Solution for Lumbar Fusion," informational brochure, Surgical Dynamics, 2 pages.

Traynelis, Vincent, et al., "Artificial Discs—The Future is Bright," www.spineuniverse.com, 5 pages (2001).

White, Augustus A, et al., "Clinical Biomechanics of the Spine," ISBN 0 397 50388 1 (1978).

Enker, P., et al.; Artificial Disc Placement, Preliminary Report With a 3-Year Minimum Follow-Up; Spine, Mar. 9, 1993; pp. 1061-1070; vol. 18; No. 8.

Hedman, Thomas, et al.; Design of an Intervertebral Disc Prosthesis; Spine Surgery; Nov. 1, 1990; pp. S256-S259.

Kostuik, John P; Intervertebral Disc Replacement, Experimental Study; Clinical Orthopedics and Related Research, 1997; pp. 27-41; No. 337.

Lee, Casey, et al.; Development of a Prosthetic Intervertebral Disc; Spine Surgery; Nov. 1, 1990; pp. S253-S255; vol. 16; No. 6.

Traynelis, Vincent, et al.; Artificial Discs—The Future is Bright; www.spineuniverse.com; Apr. 2001.

Article on PRODISC®; www.spinesolutionsinc.com.

Article on Intervertebral Dynamic Disc Spacer; www.linkspine.com; 2001.

"Biomechanics—BAK™ Interbody Fusion System" brochure; SulzerMedica, Sulzer Spine Tech; 1998.

"Patient Guide—BAK™ Interbody Fusion System" brochure; SulzerMedica, Sulzer Spine Tech; 1999.

Manufacturer Directory, ArtificialDisc.com, 2000.

Ray Threaded Fusion Cage™ informational brochure, Surgical Dynamics.

"Intervertebral Disc Replacement, Experimental Study", Kostuik, Clinical Orthopedics and Related Research, No. 337, pp. 27-41, 1997.

* cited by examiner

INTERVERTEBRAL DISC REPLACEMENT PROSTHESIS

CROSS-REFERENCE TO RELATED PATENT APPLICATION

This application is a continuation-in-part of U.S. patent application Ser. No. 10/235,117, filed Sep. 5, 2002, now issued as U.S. Pat. No. 6,964,686, entitled "INTERVERTEBRAL DISC REPLACEMENT PROSTHESIS," by Jeffrey D. Gordon, which is a continuation-in-part of and claims benefit of U.S. patent application Ser. No. 09/572,057, filed May 17, 2000, now issued as U.S. Pat. No. 6,579,321, entitled "INTERVERTEBRAL DISC REPLACEMENT PROSTHESIS," by Jeffrey D. Gordon and John M. Dawson, and which itself claims the benefit, pursuant to 35 U.S.C. §119(e), of provisional U.S. patent application Ser. No. 60/134,500, filed May 17, 1999, the contents of which are incorporated herein in their entireties by reference, respectively.

FIELD OF THE INVENTION

The present invention generally relates to a device for treatment of spine disorders, and in particular to the utilization of an intervertebral disc prosthesis to perform one or more functions of an intervertebral disc between an adjacent pair of vertebrae.

BACKGROUND OF THE INVENTION

Degenerative disc disease is a common condition of the intervertebral disc of the spine characterized by disc height collapse with or without disc herniation, osteophyte formation, foramenal stenosis, facet hypertrophy, synovial cyst, and other symptoms. Any or a combination of these findings can lead to pain or neurological deficit. Many of the symptoms of degenerative disc disease may be alleviated by decompression of the neural structures and immobilization of the involved spinal segments. Immobilization is typically achieved in the long term by removal of the disc and placement of bone graft. Temporary immobilization to encourage incorporation of the bone graft can be achieved with placement of rigid hardware such as screws and rods.

While immobilization and a successful fusion may relieve the pain associated with nerve impingement, the long-term consequences of eliminating the motion of the intervertebral disc show a tendency toward increased risk of failure of the adjacent discs. The lack of motion at the fusion site places increased biomechanical demands on the adjacent discs causing them to degenerate prematurely.

Replacement prostheses have been suggested for degenerative disc disease to allow motion at the operative disc level. Several types of artificial intervertebral discs for replacing a part or all of a removed disc have been developed, such as, ball and socket discs, and mechanical spring discs. However, these devices are devoid of stiffness and stability and rely on the remaining spinal elements, such as the ligaments, muscles and remaining intervertebral disc tissue, namely the annulus fibrosis, for stability. For example, U.S. Pat. No. 5,556,431 to Buttner-Janz, U.S. Pat. No. 5,507,846 to Bullivant and U.S. Pat. No. 5,888,226 to Rogozinski, all of which are incorporated herein by reference, disclosed prostheses that comprise ball and socket type joints. The ball and socket disc prostheses typically incorporate two plate members having cooperating inner ball and socket portions that permit articulating motion of the members during movement of the spine. These inventions rely on stretching the annulus fibrosis to put the prosthesis into compression to gain stiffness. There are a risk of altering the spine's biomechanics by increasing the disc height past the normal range and/or a risk of damage to the annulus fibrosis. If the disc space is not stretched enough an unstable spinal segment could result, possibly leading to pain and further injury. In addition, this low stiffness places detrimentally high loads on supporting ligaments and muscles, particularly during movement involving torsional rotation of the spine. Dislocation and wear are other concerns with this disc type. Implantation entails insertion of several separate pieces that must be properly aligned during surgery. The surgery is often performed with a minimal incision offering limited access to the insertion site. Perfect alignment after insertion could be difficult.

Mechanical spring discs usually incorporate one or more coiled springs disposed between metal endplates. The coiled springs preferably define a cumulative spring constant sufficient to maintain the spaced arrangement of the adjacent vertebrae and to allow normal movement of the vertebrae during flexion and extension of the spring in any direction. Disadvantages of the mechanical spring disc types include attachment of the coiled springs to the metal end plates and associated wear at the attachment points. Examples of mechanical spring discs are disclosed in U.S. Pat. No. 5,458,642 to Beer et al. and U.S. Pat. No. 4,309,777 to Patil.

Other prostheses have been suggested, for examples, see U.S. Pat. Nos. 6,136,031 and 6,296,664 to Middleton, U.S. Pat. No. 5,320,644 to Baumgartner, U.S. Pat. No. 5,827,328 to Buttermann and U.S. Pat. No. 5,676,702 to Ratron, all of which are incorporated herein by reference. These disc prostheses have their own inherent stiffness, but may not take into account that axial loads placed on the spine during activity are generally much larger than bending loads. Therefore, these prostheses would either bottom out under axial loads and offer no response to bending loads, or be stiff enough to support the axial loads and thereby too stiff to flex under bending loads.

Therefore, a heretofore unaddressed need exists in the art to address the aforementioned deficiencies and inadequacies.

SUMMARY OF THE INVENTION

In one aspect, the present invention relates to an intervertebral disc prosthesis for placement between a first vertebra and a second vertebra adjacent to the first vertebra. In one embodiment, the intervertebral disc prosthesis includes a resilient member that is arranged, in use, to be secured to the first vertebra and the second vertebra, respectively. The resilient member has a first end portion, a second end portion, and a body portion that define a cavity therebetween the first end portion and the second end portion.

The body portion of the resilient member has an axis and a slit formed therein. The slit has at least one round around the axis of the body portion. The slit also has an axis approximately coincident with the axis of the body portion. Moreover, the slit has a first end and a second end, wherein each of the first end and the second end terminates in an opening. A thickness of the slit may be either substantially constant or variable along the slit. In one embodiment of the present invention, the slit is substantially in the form of at least one helical cut formed in the body portion. In another embodiment, the slit is substantially in the form of a double helical cut formed in the body portion.

Additionally, the body portion of the resilient member may have at least one or more additional slits formed therein.

The first end portion of the resilient member includes a substantially circular edge portion and at least one engaging element protruding axially outwardly from the substantially circular edge portion to engage the first vertebra. In one embodiment the at least one engaging element has a plurality of teeth.

The second end portion of the resilient member has a substantially circular edge portion and at least one engaging element protruding axially outwardly from the substantially circular edge portion to engage the second vertebra. The at least one engaging element in one embodiment has a plurality of teeth. Moreover, the second end portion of the resilient member has a bottom portion that is defined by the first substantially planar surface, and a second, opposite substantially planar surface for engaging the substantially circular edge portion of the second end portion radially. The first substantially planar surface the second end portion of the resilient member substantially closes the cavity substantially at the substantially circular edge portion.

The intervertebral disc prosthesis further includes a first support member and a second support member. The first support member has a curved surface, a substantially planar surface and a body portion defined therebetween the curved surface and the substantially planar surface. The second support member includes a substantially planar surface, a curved surface and a body portion defined therebetween the substantially planar surface and the curved surface. The curved surface of the second support member and the curved surface of the first support member are substantially complimentary to each other. One of the curved surface of the second support member and the curved surface of the first support member comprises a convex surface, and the other comprises a concave surface that is complimentary to the convex surface.

Both of the first support member and the second support member are received in the cavity of the resilient member such that the substantially planar surface of the first support member cooperates with the first substantially planar surface of the second end portion of the resilient member, and the curved surface of the second support member cooperates with the curved surface of the first support member, respectively, for generating a motion in more than one possible direction responsive to a possible movement of at least one of the first vertebra and the second vertebra. The body portion of the second support member engages the substantially circular edge portion of the first end portion circumferentially. The substantially planar surface of the second support member substantially closes the cavity substantially at the substantially circular edge portion.

The intervertebral disc prosthesis as formed according to the present invention is able to generate a coupled motion in more than one possible direction responsive to a possible movement of at least one of the first vertebra and the second vertebra, among the resilient member, the first support member and the second support member. The motion allows extension, flexion, axial rotation and lateral bending for a wearer of the intervertebral disc prosthesis by deformation of the intervertebral disc prosthesis, whereby the first support member and the second support member communicate to act as a transferor of load generated responsive to a possible movement of at least one of the first vertebra and the second vertebra. This coupled motion among the resilient member, the first support member and the second support member, among other things, distinguishes this embodiment of the present invention from the devices that are currently available in the art.

Furthermore, the second support member is rigidly engaged with or attached to the resilient member such that in motion the resilient member, which has a spring-like stiffness, offers resistance to translation motion such that the first support member and the second support member do not "freely" translate. Additionally, in the embodiment where the first support member is rigidly engaged with or attached to the resilient member, the first support member, the second support member and the resilient member cannot "freely" translate to each other, instead, they move as a whole in a coupled motion.

In one embodiment of the present invention, the resilient member, the first support member and the second support member are made from same or different materials that are bio-compatible and surgically implantable, wherein the bio-compatible and surgically implantable materials comprise at least one of ceramic, metal, composite, or polymer materials. Furthermore, at least one of the resilient member, the first support member and the second support member has a wear reducing coating such as diamond-like coating.

In another aspect, the present invention relates to an intervertebral disc prosthesis for placement between a first vertebra and a second vertebra adjacent to the first vertebra. In one embodiment, the intervertebral disc prosthesis includes a resilient member and a first support member. The resilient member is arranged, in use, to be secured to the first vertebra and the second vertebra, respectively.

The resilient member has a first end portion, a second end portion, and a body portion that define a cavity therebetween the first end portion and the second end portion with an axis Z, wherein the second end portion includes a bottom portion that substantially closes the cavity at the second end portion, the bottom portion has a first surface and a second, opposite surface. Furthermore, the resilient member includes a bellows member. The bellows member may have a slit formed therein.

The first support member has a first surface, a second surface and a body portion defined therebetween. The first support member is received in the cavity of the resilient member such that the second surface of the first support member cooperates with the first surface of the bottom portion of the resilient member, for generating a motion in more than one possible direction responsive to a possible movement of at least one of the first vertebra and the second vertebra.

In one embodiment, one of the first surface and the second surface of the first support member has a curved surface, and the other has a substantially planar surface. Cooperation of the second surface of the first support member with the first surface of the bottom portion of the resilient member allows the support member to move axially along the axis Z, translate radially, rotate around the axis Z, and rotate around an axis that is different from the axis Z.

Moreover, the intervertebral disc prosthesis includes at least one engaging element protruding axially outwardly from the first end portion to engage the first vertebra in use, wherein the at least one engaging element comprises a plurality of teeth. Furthermore, the at least one engaging element has additional engaging means associated with the at least one engaging element to engage the first vertebra in use, wherein the additional engaging means comprises a tab member. Additionally, the intervertebral disc prosthesis includes at least one engaging element protruding axially outwardly from the second end portion to engage the second vertebra in use, wherein the at least one engaging element comprises a plurality of teeth. The at least one engaging element further has additional engaging means associated with the at least one engaging element to engage the second vertebra in use, wherein the additional engaging means comprises a tab member.

In yet another aspect, the present invention relates to an intervertebral disc prosthesis for placement between a first vertebra and a second vertebra adjacent to the first vertebra. In one embodiment, the intervertebral disc prosthesis includes a resilient member that is arranged, in use, to be secured to the first vertebra and the second vertebra, respectively. The resilient member has a first end portion, a second end portion, and a body portion defining a cavity therebetween the first end portion and the second end portion with an axis Z, wherein the second end portion includes a bottom portion that substantially closes the cavity at the second end portion. The resilient member further has a bellows member. The bellows member includes at least one helical cut so as to enable the resilient member to move in more than one possible direction responsive to a possible movement of at least one of the first vertebra and the second vertebra. The more than one possible direction includes the axis Z, at least one additional axis that is perpendicular to the axis Z, and a third axis that is perpendicular to the axis Z and the at least one additional axis. The possible motions include extension, flexion, axial rotation and lateral bending.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE PREFERRED EMBODIMENTS

Figure 1:
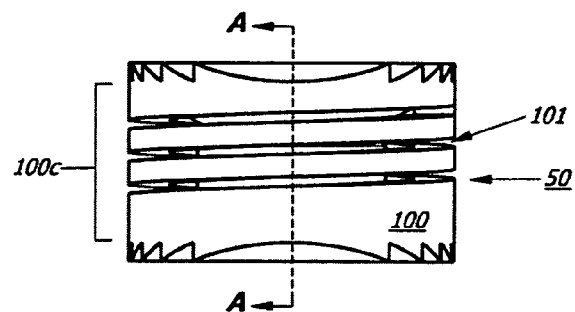
FIG. 1 shows a side view of an intervertebral disc prosthesis according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

The description will be made as to the embodiments of the present invention in conjunction with the accompanying drawings 1-24. In accordance with the purposes of this invention, as embodied and broadly described herein, this invention, in one aspect, relates to an intervertebral disc prosthesis for placement between a first vertebra and a second vertebra adjacent to the first vertebra.

Figure 2:
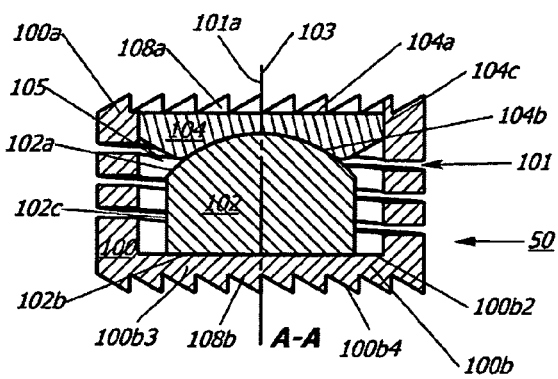
FIG. 2 shows a cross-sectional view of the intervertebral disc prosthesis along line A-A of FIG. 1.
Figure 3:
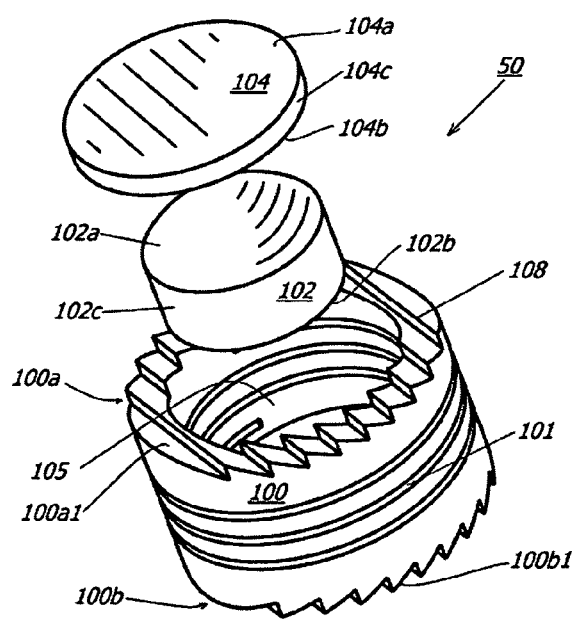
FIG. 3 shows an exploded view of the intervertebral disc prosthesis, as shown in FIGS. 1 and 2.

Referring in general to FIGS. 1-6, and in particular to FIGS. 1-3 first, an intervertebral disc prosthesis 50 in one embodiment has a resilient member 100 that is arranged, in use, to be secured to a first vertebra 200 and a second vertebra 202, respectively. The resilient member 100 includes a first end portion 100a, a second end portion 100b, and a body portion 100c defining a cavity 105 therebetween the first end portion 100a and the second end portion 100b.

The first end portion 100a of the resilient member 100 includes a substantially circular edge portion 100a1 and at least one engaging element protruding axially outwardly from the substantially circular edge portion 100a1 to engage the first vertebra 200.

The second end portion 100b of the resilient member 100 has a first substantially planar surface 100b2, a second, opposite substantially planar surface 100b4, and a bottom portion 100b3 that is defined by the first substantially planar surface 100b2 and the second substantially planar surface 100b4. Furthermore, the second end portion 100b of the resilient member 100 has a substantially circular edge portion 100b1 and at least one engaging element protruding axially outwardly from the substantially circular edge portion 100b1 to engage the second vertebra 202. The bottom portion 100b3 engages the substantially circular edge portion 100b1 of the second end portion 100b of the resilient member 100 radially. The first substantially planar surface 100b2 substantially closes the cavity 105 of the resilient member 100 substantially at the substantially circular edge portion 100b1.

The body portion 100c of the resilient member 100 has an axis 103 and a slit 101 formed therein the body portion 100c. The slit 101 has at least one round around the axis 103. The slit 101 also has an axis 101a approximately coincident with the axis 103 of the body portion 100c. Additionally, the slit 101 has a first end and a second end, where each of the first end and the second end terminates in an opening as shown, for example, more clearly in FIG. 7. A thickness of the slit 101 can be either substantially constant or variable along the slit 101. The slit 101 in one embodiment is substantially in the form of at least one helical cut formed in the body portion 100c. In another embodiment, the slit 101 is substantially in the form of a double helical cut formed in the body portion 100c. Furthermore, the body potion 100c of the resilient member 100 has at least one more slit formed therein in addition to the slit 101.

The resilient member 100 resembles a helical coil or spring such that it allows the intervertebral disc prosthesis 50 to react to bending loads by flexing. The geometry of the helical slit 101 can determine the stiffness of the resilient member 100 and therefore the stiffness of the intervertebral disc prosthesis 50. For example, to produce a more flexible implant the thickness of the helical slit 101 can be increased so that less material of the resilient member 100 remains. The number of rounds affects the stiffness of the resilient member 100 as well. The spring action of the resilient member 100 will allow rotation and will have an inherent torsional stiffness that is also affected by the geometry of the helical slit 101. The range of motion of the intervertebral disc prosthesis 50 is affected by the point at which the resilient member 100 bottoms out, that is, the point at which a bending load causes adjacent rounds to come into contact. The range of motion is affected by the space between the rounds, which is equivalent to the thickness of helical slit 101 multiplied by the number of rounds. Therefore, the helical slit 101 can be tailored to match the mechanical and kinematical characteristics of a normal disc at any level in the spine.

The intervertebral disc prosthesis 50 further includes a first support member 102 and a second support member 104. The first support member 102 has a curved surface 102a, a substantially planar surface 102b and a body portion 102c defined therebetween the curved surface 102a and the substantially planar surface 102b. The second support member 104 has a substantially planar surface 104a, a curved surface 104b and a body portion 104c defined therebetween the substantially planar surface 104a and the curved surface 104b. The curved surface 102a of the first support member 102 and the curved surface 104b of the second support member 104 are substantially complimentary to each other, wherein one of the curved surface 102a of the first support member 102 and the curved surface 104b of the second support member 104 has a convex surface, and the other has a concave surface that is complimentary to the convex surface. In one embodiment, the curved surface 102a of the first support member 102 is a convex surface while the curved surface 104b of the second support member is a concave surface that is substantially complementary to the convex surface 102a of the first support member 102, as shown in FIG. 2.

Both of the first support member 102 and the second support member 104 of the intervertebral disc prosthesis 50 are received in the cavity 105 of the resilient member 100 such that the substantially planar surface 102b of the first support member 102 cooperates with the first substantially planar surface 100b2 of the second end portion 100b of the resilient member 100, and the curved surface 104b of the second support member 104 cooperates with the curved surface 102a of the first support member 102, respectively, for generating a motion in more than one possible direction responsive to a possible movement of at least one of the first vertebra 200 and the second vertebra 202. The body portion 104c of the second support member 104 engages the substantially circular edge portion 100a1 of the first end portion 100a of the resilient member 100 radially. The substantially planar surface 104a of the second support member 104 substantially closes the cavity 105 substantially at the substantially circular edge portion 100a1. The first support member 104 may be rigidly attached to the resilient member 100 by press-fit, threads, retaining ring, pins, welding or some other means known to people skilled in the art.

As assembled according to the present invention, the intervertebral disc prosthesis 50 can generate a coupled motion in more than one direction responsive to a possible movement of at least one of the first vertebra 200 and the second vertebra 202, among the resilient member 100, the first support member 102 and the second support member 104. The coupled motion allows extension, flexion, axial rotation and lateral bending for a wearer of the intervertebral disc prosthesis 50 by deformation of the intervertebral disc prosthesis 50. Specifically, cooperation of the substantially planar surface 102b of the first support member 102 with the first substantially planar surface 100b2 of the second end portion 100b of the resilient member 100 may permit the first support member 102 to move translationally with respect to the resilient member 100. The ball-and-socket communication mechanism between the first support member 102 and the second support member 104 enables the second support member 104 to rotate with respect to the first support member 104 around three orthogonal axes including the axis 103. The resilient member 100 is itself capable of moving along the axis 103 and rotating (bending) around an additional axis that is perpendicular to the axis 103 and an axis that is perpendicular to both the axis 103 and the additional axis. Furthermore, The ball-and-socket communication mechanism between the first support member 102 and the second support member 104 provides support to the intervertebral disc prosthesis 50, which acts as a transferor of axial compression loads.

Figure 6:
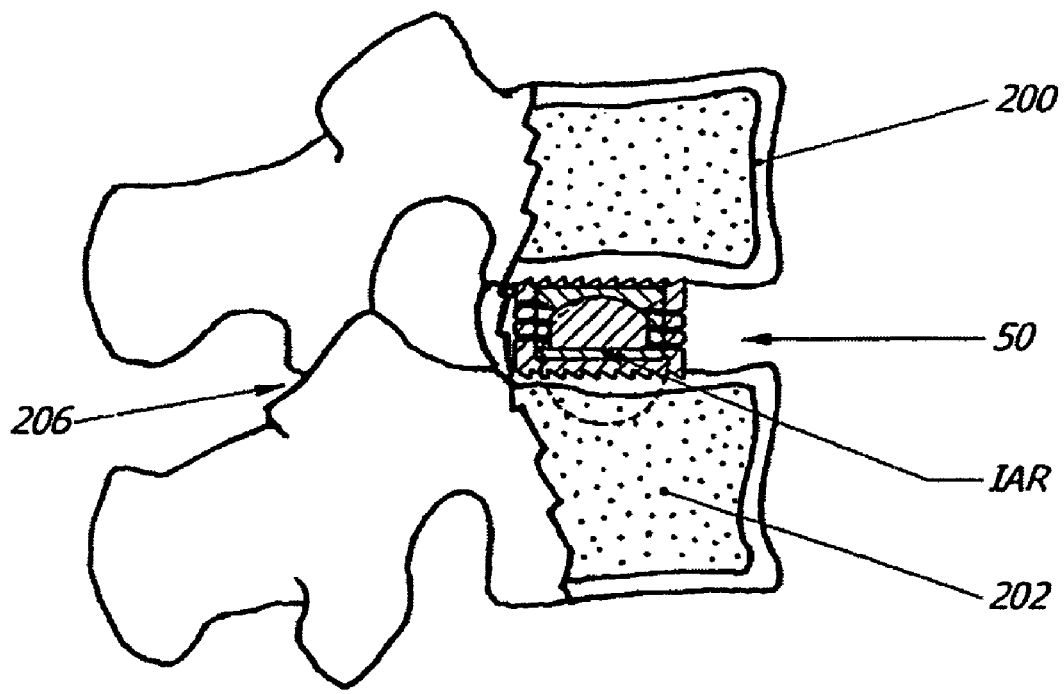
FIG. 6 shows a cross-sectional side view of a spinal motion segment having an intervertebral disc prosthesis placed in an intervertebral disc space according to one embodiment of the present invention.

In use, as schematically shown in FIG. 6, the intervertebral disc prosthesis 50 is placed between the first vertebra 200 and the second vertebra 202 such that the substantially planar surface 104a of the second support member 104 communicates with the first vertebra 200 and the second substantially planar surface 100b4 of the second end portion 100b of the resilient member 100 communicates with the second vertebra 202, respectively. Attachment of the intervertebral disc prosthesis 50 to both the first vertebra 200 and the second vertebra 202 involves both immediate and long-term fixation. In one embodiment, immediate fixation can be achieved with a mechanical bone attachment means. For example, as shown in FIGS. 1-3, the at least one engaging element protruding axially outwardly from the substantially circular edge portion 100a1 of the first end portion 100a of the resilient member 100 surfaces may include a plurality of teeth 108a to engage the first vertebra 200. The at least one engaging element protruding axially outwardly from the substantially circular edge portion 100b1 of the second end portion 100b of the resilient member 100 surfaces may include a plurality of teeth 108b to engage the second vertebra 202. Additionally, the substantially planar surface 104a of the second support member 104, the second substantially planar surface 100b4 the second end portion 100b of the resilient member 100 including teeth 108a and 108b can be coated with a bone ingrowth inducing osteoconductive substance such as sintered beads or sintered wires or an osteoinductive coating such as hydroxyapatite for long-term fixation. Osteoinductive and osteoconductive coatings have been used extensively in joint replacement for many years and have been proven to be effective.

The resilient member 100, the first support member 102 and the second support member 104 can be made from same or different materials that are bio-compatible and surgically implantable, wherein the bio-compatible and surgically implantable materials include at least one of ceramic, metal, composite, or polymer materials. The preferred material for the resilient member 100 should possess high fatigue strength such as cobalt chrome alloy, titanium, titanium alloy, stainless steel, or the like. The material for the first support member 102 and the second support member 104 should possess excellent wear resistance and compressive strength. Ceramics, titanium, titanium alloy, stainless steel, cobalt chrome, alloy composites, or polymers should preferably be used for these elements. Alternatively, a biocompatible material with a wear reducing coating can be utilized. For example, a titanium nitride coating may be used on the supports or the resilient member. In one embodiment, at least one of the resilient member 100, the first support member 102 and the second support member 104 has a coating that includes a titanium nitride material.

Figure 4:
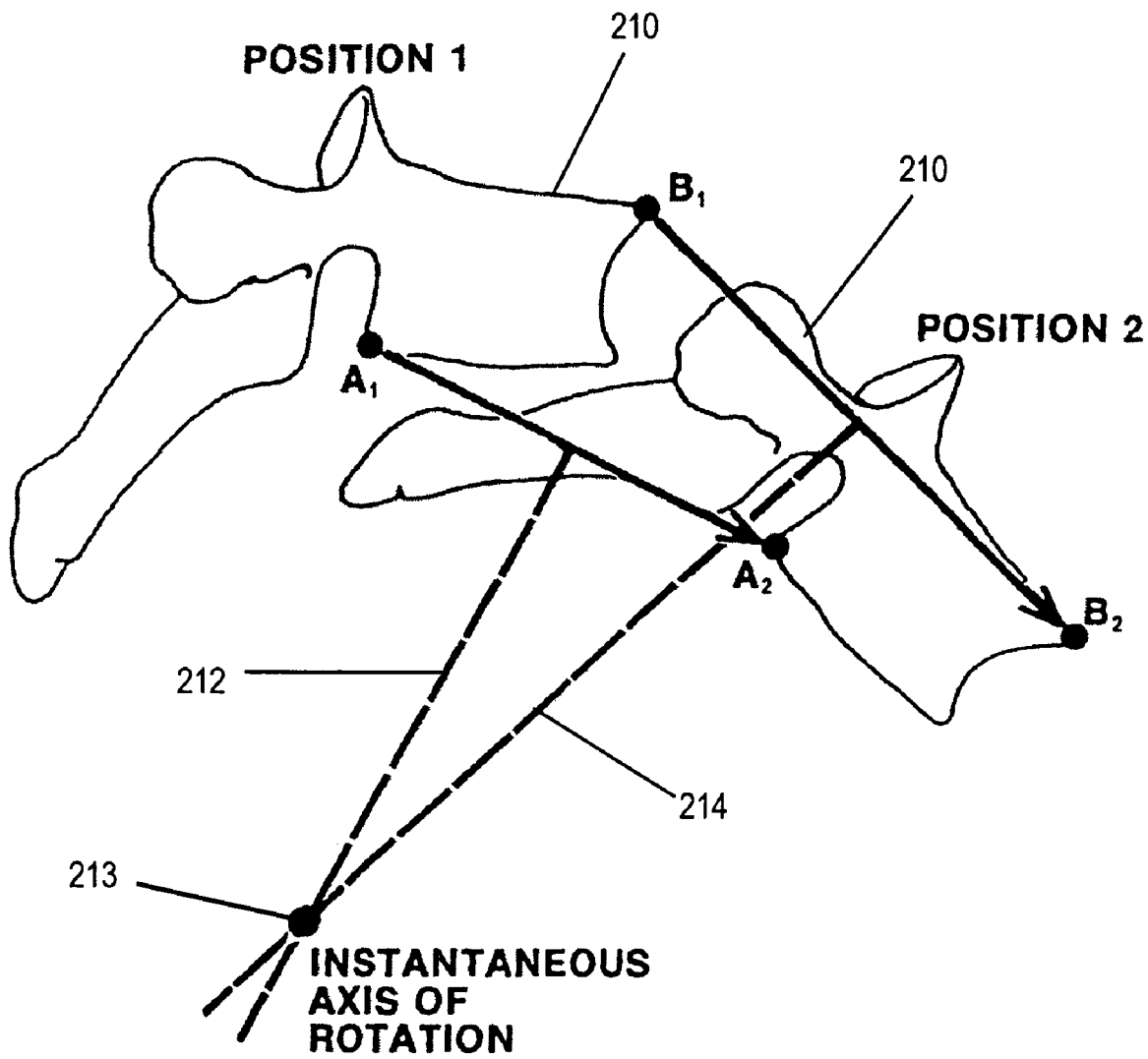
FIG. 4 schematically shows a method for finding an instantaneous axis of rotation of a vertebra in motion relative to a fixed point.

The instantaneous axis of rotation (IAR) is a parameter that characterizes how one body rotates with respect to another body (or a fixed point) in planar motion. Normal spinal motion can be characterized as planar (2-dimesional) for pure flexion-extension. FIG. 4 demonstrates a general method for determining the IAR of the motion of a body from two positions. For instance, a body (a vertebra) 210 is initially at POSITION 1 having two points $A_1$ and $B_1$, after a motion, the body 210 is located at POSITION 2. Points $A_1$ and $B_1$ move to corresponding points $A_2$ and $B_2$, respectively in the POSITION 2. As a result, a translation vector $A_1$-$A_2$ of point $A_1$ of the body 210 is directed from point $A_1$ to point $A_2$ and has a bisector 212 perpendicular to the translation vector $A_1$-$A_2$. A translation vector $B_1$-$B_2$ of point $B_1$ of the body 210 is directed from point $B_1$ to point $B_2$ and has a bisector 214 perpendicular to the translation vector $B_1$-$B_2$. Both the translation vector $A_1$-$A_2$ and the translation vector $B_1$-$B_2$ constitutes a plane of the motion. An axis at an intersection 213 of the bisectors 212 of the translation vector $A_1$-$A_2$ and the bisectors 214 of the translation vectors $B_1$-$B_2$ is the IAR of the motion that is perpendicular to the plane of the motion.

The intervertebral disc prosthesis 50 in one embodiment of the present invention may incorporate a mobile IAR. In one embodiment as shown in FIGS. 1-3, the curved surface 102a of the first support member 102 can be a convex surface, and the curved surface 104b of the second support member 104 correspondingly has a surface suitable for receiving and communicating with the convex surface of the first support member 102. The convex surface of the first support member 102 may vary. For instance, it may range from a partial hemisphere to a full hemisphere or it may be an elongated element with a rounded or partially rounded end. Motion at the interface between the first support member 102 and the second support member 104 has an IAR at the center of the radius of the bearing surface of the first support member 102. This embodiment, as shown in FIG. 2, also allows translation between the first support member 102 and the resilient member 100. The combination of rotation and translation allows a range of possible IARs.

Figure 5:
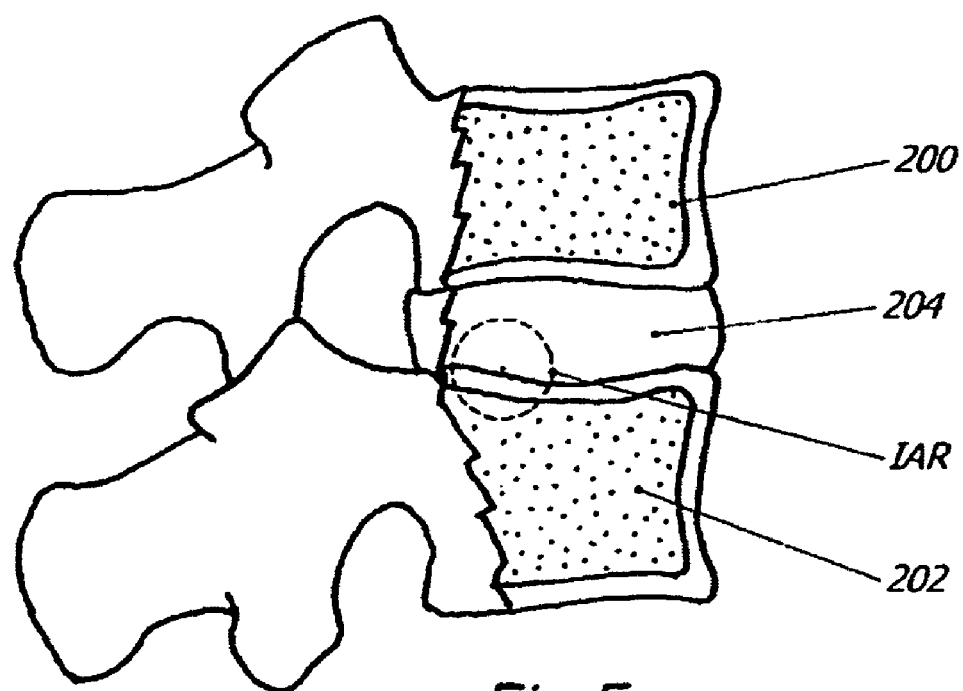
FIG. 5 shows a cross-sectional side view of a normal spinal motion segment.

Referring now to FIG. 5, a cross-sectional view of a motion segment including a first vertebra 200, an intervertebral disc (IVD) 204 and a second vertebra 202 is shown. An IAR for the adjacent vertebrae 200 and 202 in the normal lumbar spine is located on and/or near the superior endplate of the second vertebra 202 of the motion segment, as shown in FIG. 5. FIG. 6 shows the same cross-section view of the motion segment as FIG. 5, but with replacement of the intervertebral disc 204 with an intervertebral disc prosthesis 50 of the present invention. In order to prevent unnatural loading of facet joints 206, the IAR of the motion segment for the adjacent vertebrae 200 and 202 must be maintained in the same area as the one without replacing the intervertebral disc 204, as shown in FIG. 5. The mobile IAR described above allows the IAR of the motion between the first vertebra 200 and the second vertebra 202 to be substantially maintained at the same position after implantation of the intervertebral disc prosthesis 50.

Figure 7:
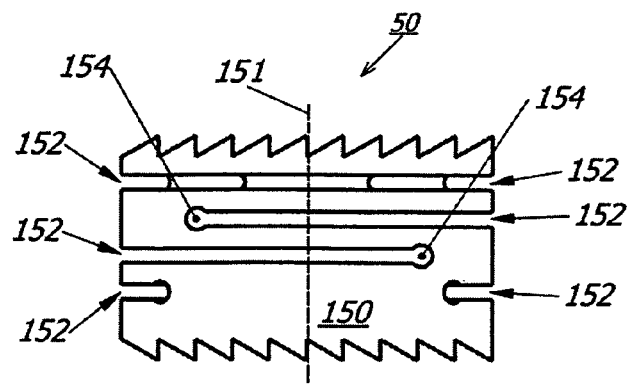
FIG. 7 shows a side view of an intervertebral disc prosthesis according to one embodiment of the present invention.
Figure 8:
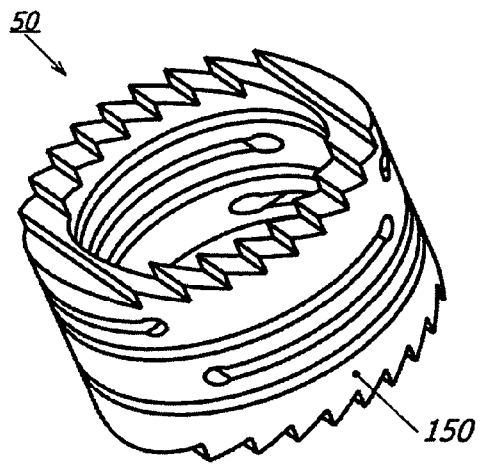
FIG. 8 shows a perspective view of the intervertebral disc prosthesis as shown in FIG. 7.

Referring to FIGS. 7 and 8, an intervertebral disc prosthesis 50 according to an alternative embodiment of the present invention includes a resilient member 150 with an axis 151. The resilient member 150 has a plurality of perimeter slits 152 cut therein, where the plurality of perimeter slits 152 is approximately horizontal, instead of a helical-type slit, as shown in FIGS. 1-3. Preferably, each of the plurality of perimeter slits 152 is substantially at a right angle relative to the axis 151 of the resilient member 150. The perimeter slits 152 are orientated such that at least one slit is opened and at least one slit is closed under an action of bending loads imposed at any plane through the axis 151 of the resilient member 150. In the embodiment as shown in FIGS. 7 and 8, the plurality of perimeter slits 152 includes three perimeter slits. Each of the plurality of perimeter slits 152 terminates in a hole or a perimeter opening 154, with a diameter that is larger than the thickness of the slit so as to reduce stress concentration. In one embodiment, the perimeter opening 154 is circular-shaped. The depth, thickness and number of the perimeter slits 152 as well as the size of perimeter opening 154 affect the stiffness of the intervertebral disc prosthesis 50. The thickness and number of the perimeter slits 152 affect the range of motion of the intervertebral disc prosthesis 50.

Figure 9:
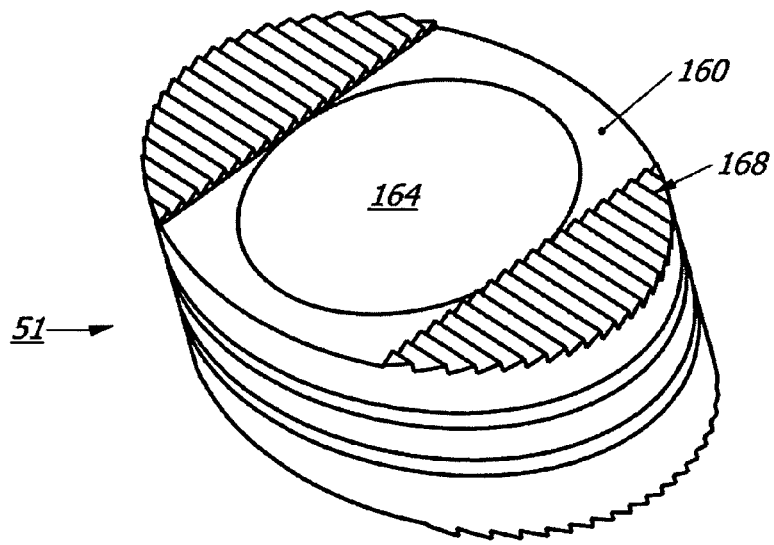
FIG. 9 shows a perspective view of an intervertebral disc prosthesis according to another embodiment of the present invention.

An intervertebral disc prosthesis can be made into a variety of shapes, as long as the spirit of the invention is not adversely affected. That is, the intervertebral disc prosthesis of the present invention may have a surface, such as, for example, the upper surface or the lower surface, which is flat, convex in shape or is otherwise shaped to fit the cavity of a vertebral endplate. Furthermore, from a top view, the intervertebral disc prosthesis may be of a variety of shapes, for instance, circular, kidney-shaped, or oval-shaped. FIG. 9 shows an alternative embodiment of an intervertebral disc prosthesis 51 including a resilient member 160 that is oval shaped. A plurality of teeth 168 protrudes axially outwardly from one end portion of the resilient member 160 for engaging one of the first vertebra 200 and the second vertebra 202. A support member 164 provides the flexibility for the intervertebral disc prosthesis 51 to generate a motion in more than one direction responsive to a possible movement of at least one of the first vertebra 200 and the second vertebra 202.

Figure 10:
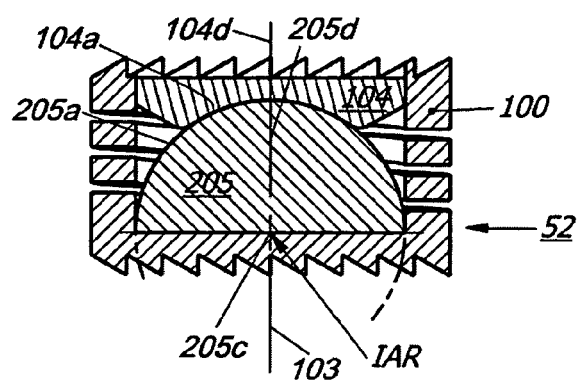
FIG. 10 shows a cross-sectional side view of an intervertebral disc prosthesis according to one embodiment of the present invention.

Referring now to FIGS. 10-16, an intervertebral disc prosthesis is shown according to other embodiments of the present invention. FIG. 10 shows a cross-sectional view of an intervertebral disc prosthesis 52 in one embodiment, which has a resilient member 100 with an axis 103, a first support member 205 and a second support member 104. The first support member 205 is a full hemisphere that has a symmetrical axis 205d and is sized to fit into the resilient member 100. The second support member 104 includes a concave surface 104b having a symmetrical axis 104d and is substantially complementary to a convex surface 205a of the full hemisphere of the first support member 205. As assembled, both of the symmetrical axis 205d of the first support member 205 and the symmetrical axis 104d of the concave surface 104b of the second support member 104 are substantially coincident with the axis 103 of the resilient member 100. In the embodiment, a fixed IAR is located at the center 205c of the radius of the full hemisphere of the first support member 205 that is on the axis 103 of the resilient member 100.

Figure 11:
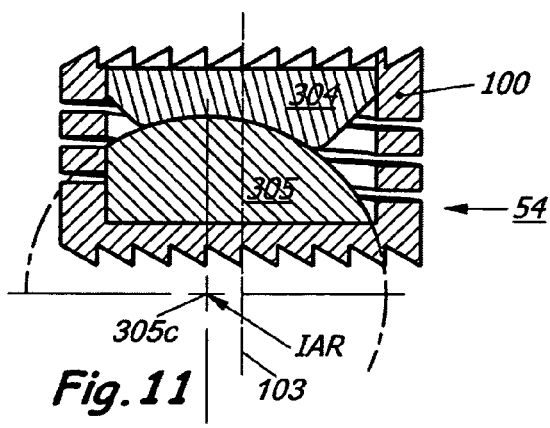
FIG. 11 shows a cross-sectional side view of an intervertebral disc prosthesis according to another embodiment of the present invention.

FIG. 11 shows a cross-sectional view of an alternative embodiment of an intervertebral disc prosthesis 54 of the present invention that has a resilient member 100 with an axis 103, a first support member 305 and a second support member 304. The first support member 305 is a partial hemisphere such that when the first support member 305 is received in the resilient member 100 the center 305c of the radius of the partial hemisphere is displaced from the axis 103 of the resilient member 100. The second support member 304 is configured to communicate with the partial hemispherical of the first support member 305. In such embodiment, the IAR is located at 305c, as shown in FIG. 10. The embodiment of the intervertebral disc prosthesis 54 of the present invention demonstrates that the LAR of an intervertebral disc prosthesis can be tailored to match the IAR of a healthy intervertebral disc simply by altering the radius of curvature and the center of the radius of curvature of a partial hemispherical, first support member 305.

Figure 12:
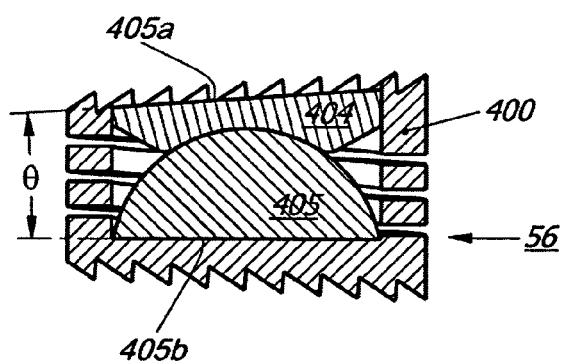
FIG. 12 shows a cross-sectional side view of an intervertebral disc prosthesis according to yet another embodiment of the present invention.

FIG. 12 shows an angulated intervertebral disc prosthesis 56 with an angulated resilient member 400 and an augmented first support member 405 and an augmented second support member 404. In the embodiment of the intervertebral disc prosthesis 56, the resilient member 400 has a height varying continuously from a longest size at one side to a shortest size at an oppose side such that when the first support member 405 and the second support member 404 are received in the resilient member 400, a planar surface 404a of the second support member 404 and a planar surface 405b of the first support member 405 have a angle θ. The angle θ incorporated into the angulated intervertebral disc prosthesis 56 is meant to maintain a natural lordosis of the lumbar or cervical spine or a natural kyphosis of the thoracic spine. This angle could be matched to any lordosis or kyphosis of an intervertebral disc level being replaced.

Figure 13:
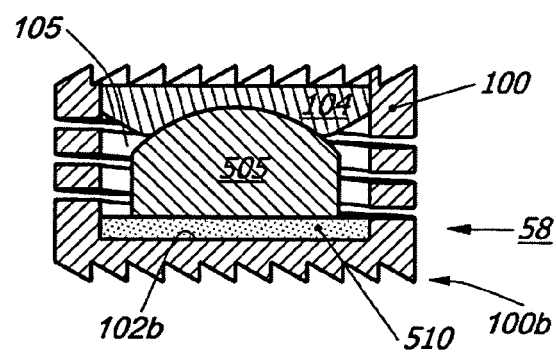
FIG. 13 shows a cross-sectional side view of an intervertebral disc prosthesis according to an alternative embodiment of the present invention.

FIG. 13 shows an alternative embodiment of an intervertebral disc prosthesis 58 of the present invention. The intervertebral disc prosthesis 58 includes a resilient member 100, a first support member 505, a second support member 104, and a lower seat member 510. The resilient member 100 has a cavity 105 and a bottom portion 100b having an inner surface 102b. The first support member 505, the second support member 104, and the lower seat member 510 are housed into the cavity 105 of the resilient member 100 such that the lower seat member 510 is placed between the first support member 505 and the inner surface 102b of the bottom portion 100b of the resilient member 100 for communicating with the first support member 510, and the second support member 104 communicates with the first support member 505 for generating a motion in more than one direction respective to a possible movement of at least one of the first vertebra 200 and the second vertebra 202. The resilient member 100 may be made of a metal material, the first support member 505 and second support member 104 may be made of a ceramic material having a predetermined rigidity, and the lower seat member 510 may also be made of the ceramic so that all elements experiencing sliding contact would gain the advantage of low wear ceramic on ceramic contact.

Figure 14:
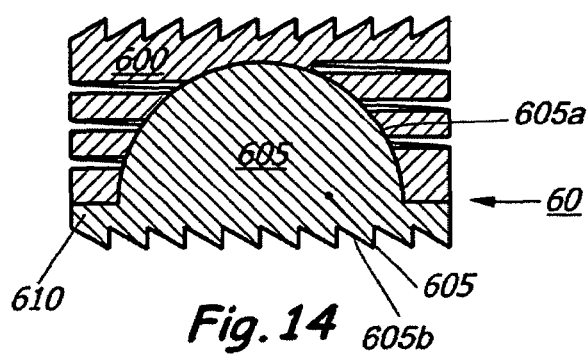
FIG. 14 shows a cross-sectional side view of an intervertebral disc prosthesis according to one embodiment of the present invention.

Another alternative embodiment of an intervertebral disc prosthesis 60 of the present invention is shown in FIG. 14. The intervertebral disc prosthesis 60 includes a resilient member 600 having a concave recess formed therein, and a first support member 605. The first support member 605 includes a first surface 605a, a second surface 605b and a flange 610 radially outwardly extending from an edge portion of the second surface 605b, where the first surface 605a is a convex surface that is complementary to and communicated with a surface of the concave recess of the resilient member 600. In this embodiment, a second support member is incorporated into the resilient member 600. The resilient member 600 may be rigidly attached to the flange 610 of the first support member 605 by welding, pins, retaining ring or some other means known to people skilled in the art.

Figure 15:
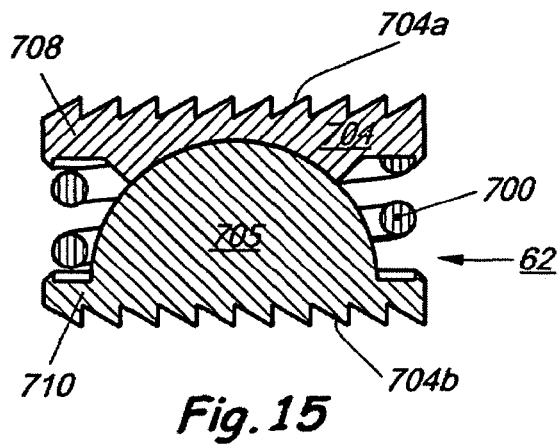
FIG. 15 shows a cross-sectional side view of an intervertebral disc prosthesis according to another embodiment of the present invention.

An intervertebral disc prosthesis 62 having a resilient member 700, a first support member 705 and a second support member 704 is shown in FIG. 15 according to another embodiment of the present invention. The resilient member 700 includes a spring element that is a conventional helical spring made by forming a wire into a helix. The first support member 705 has a surface 705b and a flange 710 radially outwardly extending from an edge portion of the surface 705b. The second support member 704 has a surface 704a and a flange 708 radially outwardly extending from an edge portion of the surface 704a. The first support member 705 and the second support member 704 are made to communicate with each other and to communicate with the resilient member 700 for generating a motion in more than one direction respective to a possible movement of at least one of the first vertebra 200 and the second vertebra 202. The resilient member 700 may be rigidly attached to both the first support member 705 and the second support member 704.

Figure 16:
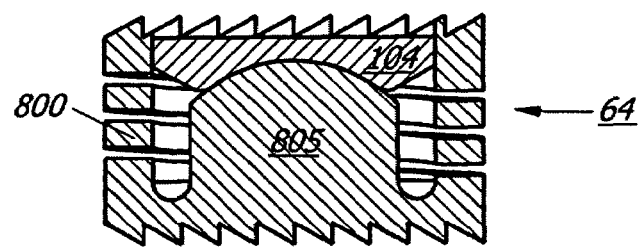
FIG. 16 shows a cross-sectional side view of an intervertebral disc prosthesis, according to yet another embodiment of the present invention.

FIG. 16 shows an intervertebral disc prosthesis 64 according to one embodiment of the present invention. The intervertebral disc prosthesis 64 includes a resilient member 800 and a upper disc support member 104. The resilient member 800 has a protuberance 805 that serves as a lower disc support member. The upper disc support member 104 is made to communicate with the protuberance 805 such that when assembled, the intervertebral disc prosthesis 64 enables o generate a motion in more than one direction respective to a possible movement of at least one of the first vertebra 200 and the second vertebra 202.

Figure 17:
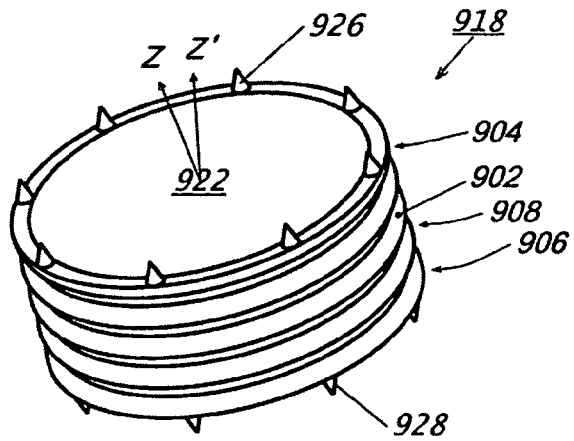
FIG. 17 shows a perspective view of an intervertebral disc prosthesis according to one embodiment of the present invention.
Figure 18:
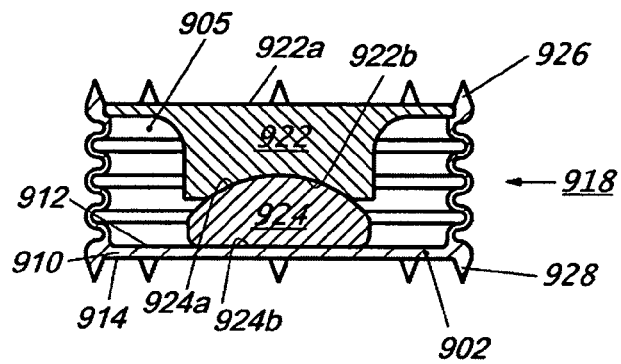
FIG. 18 shows a cross-sectional side view of the intervertebral disc prosthesis as shown in FIG. 17.

Referring now to FIGS. 17 and 18, an intervertebral disc prosthesis 918 according to an alternative embodiment of the present invention includes a resilient member 902, a first support member 924 and a second support member 922. The resilient member 902 has a first end portion 904, a second end portion 906, and a body portion 908 defining a cavity 905 therebetween the first end portion 904 and the second end portion 906 with an axis Z. The body portion 908 includes a bellows member made by welding, hydroforming or other means known to people skilled in the art. The second end portion 906 includes a bottom portion 910 that substantially closes the cavity 905, where the bottom portion 910 has a first surface 912 and a second, opposite surface 914.

The resilient member 902 is arranged, in use, to be secured to a first vertebra 200 and a second vertebra 202, respectively. In the embodiment, as shown in FIGS. 17 and 18, the first end portion 904 of the resilient member 902 has at least one engaging element protruding axially outwardly from the first end portion 904 to engage the first vertebra 200 in use, where the at least one engaging element has a plurality of teeth 926. The second end portion 906 of the resilient member 902 has at least one engaging element protruding axially outwardly from the second end portion 906 to engage the second vertebra 202 in use, where the at least one engaging element includes a plurality of teeth 928.

The first support member 924 has a first surface 924a, a second surface 924b and a body portion defined therebetween. In one embodiment, the first surface 924a is a curved surface and the second surface 924b is a substantially planar surface. The second support member 922 has a first surface 922a, a second surface 922b and a body portion defined therebetween. As formed, one of the first surface 922a and the second surface 922b of the second support member 922 is a curved surface, and the other is a substantially planar surface. The first surface 924a of the first support member 924 and the second surface 922b of the second support member 922 are complimentary to each other such that one of them is a convex surface, and the other will be a concave surface that is complimentary to the convex surface.

Both the first support member 924 and the second support member 922 are received in the cavity 905 of the resilient member 902 such that the second surface 924b of the first support member 924 cooperates with the first surface 912 of the bottom portion 910 of the resilient member 902 and the second surface 922b of the second support member 922 cooperates with the first surface 924a of the first support member 924, for generating a motion in more than one possible direction responsive to a possible movement of at least one of the first vertebra 200 and the second vertebra 202. This configuration allows the intervertebral disc prosthesis 918 to move axially along the axis Z, translate radially, rotate around the axis Z, and rotate around an axis Z' that is different, or apart, from the axis Z. As assembled, the second support member 922 may be rigidly attached to the resilient member 902 or attached with the ability to rotate with respect to the resilient member 902 about the axis Z of the resilient member 902. The attachment of the second support member 922 to the resilient member 902 substantially closes the cavity 905 at the first end portion 904 of the resilient member 902.

Figure 19:
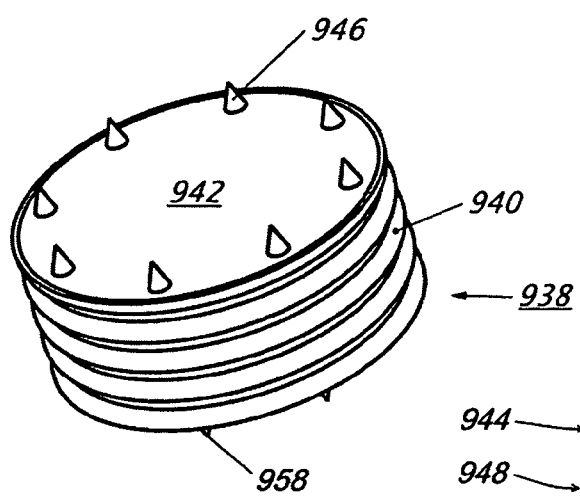
FIG. 19 shows a perspective view of an intervertebral disc prosthesis according to another embodiment of the present invention.
Figure 20:
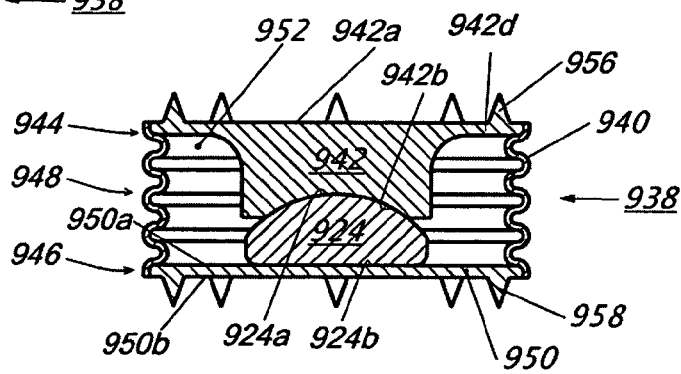
FIG. 20 shows a cross-sectional side view of the intervertebral disc prosthesis as shown in FIG. 19.

FIGS. 19 and 20 show another embodiment of intervertebral disc prosthesis 938 of the present invention, where the intervertebral disc prosthesis 938 includes a resilient member 940, a first support member 924, a second support member 942 and a plate 950. The resilient member 940 has a first end portion 944, a second end portion 946, and a body portion 948 defining a cavity 952 therebetween the first end portion 944 and the second end portion 946 with an axis Z. The body portion 948 includes a metal bellows member made by welding, hydroforming or other means. The plate 950 having a first surface 950a and a second surface 950b may be rigidly attached to the second end portion 946 of the resilient member 940 or attached with the ability to rotate with respect to the resilient member 940 about the axis Z of the resilient member 940. The attachment of the plate 950 to the resilient member 940 substantially closes the cavity 952 at the second end portion 946 of the resilient member 940.

The first support member 924 has a curved surface 924a and a planar surface 924b. The second support member 942 has a curved surface 942b, a planar surface 942a and a flange 942d radially outwardly extending from an edge portion of the planar surface 942a. In the example, as shown in FIGS. 19 and 20, the curved surface 924a of the first support member 924 is a convex surface, while the curved surface 942b of the second support member 942 is a concave surface that is complimentary to the convex surface 924a.

Both the first support member 924 and the second support member 942 are received in the cavity 952 of the resilient member 940 such that the planar surface 924b of the first support member 924 cooperates with the first surface 950a of the plate 950 and the curved surface 942b of the second support member 942 cooperates with the curved surface 924a of the first support member 942, for generating a motion in more than one possible direction responsive to a possible movement of at least one of the first vertebra 200 and the second vertebra 202. As assembled, the flange 942d of the second support member 942 may be rigidly attached to the resilient member 940 at the first end portion 944 or attached with the ability to rotate with respect to the resilient member 940 about the axis Z of the resilient member 940 such that the planar surface 942a of the second support member 942 closes the cavity 952 at the first end portion 944 of the resilient member 940.

The resilient member 940 is arranged, in use, to be secured to a first vertebra 200 and a second vertebra 202, respectively. In the embodiment of the intervertebral disc prosthesis 938, as shown in FIGS. 19 and 20, the planar surface 942a of the second support member 942 has at least one engaging element protruding axially outwardly from the planar surface 942a to engage the first vertebra 200 in use, where the at least one engaging element has a plurality of teeth 956. The second surface 950b of the plate 950 has at least one engaging element protruding axially outwardly from the second surface 950b to engage the second vertebra 202 in use, where the at least one engaging element includes a plurality of teeth 958.

Figure 21:
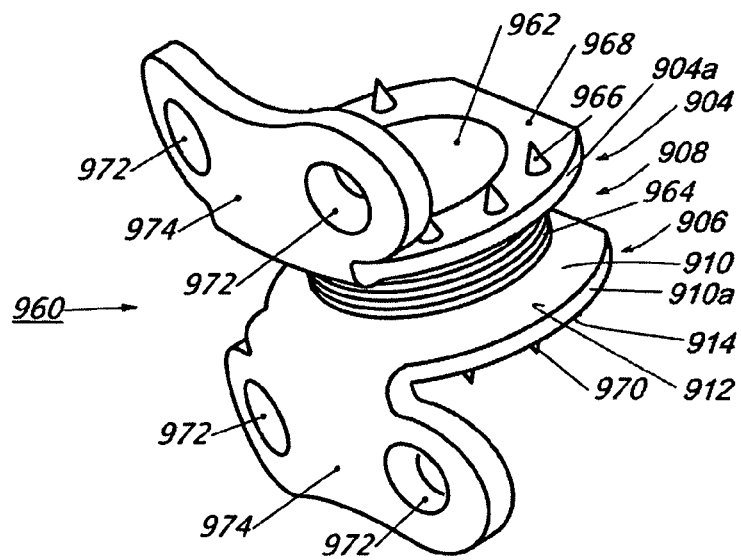
FIG. 21 shows a perspective view of an intervertebral disc prosthesis according to yet another embodiment of the present invention.
Figure 22:
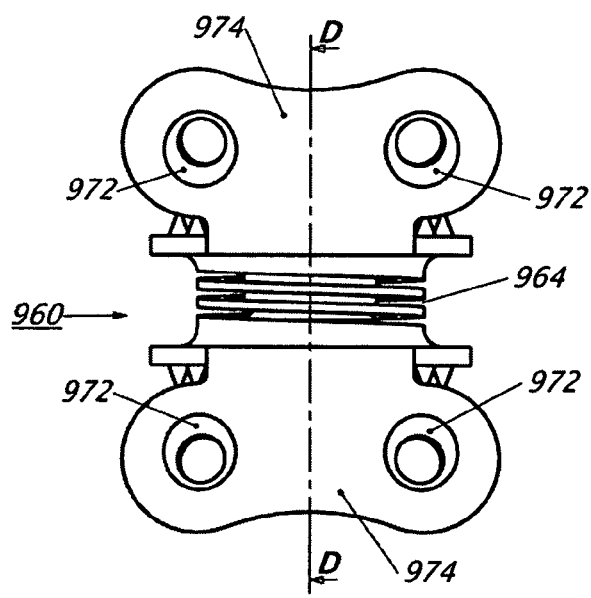
FIG. 22 shows a front side view of the intervertebral disc prosthesis as shown in FIG. 21.
Figure 23:
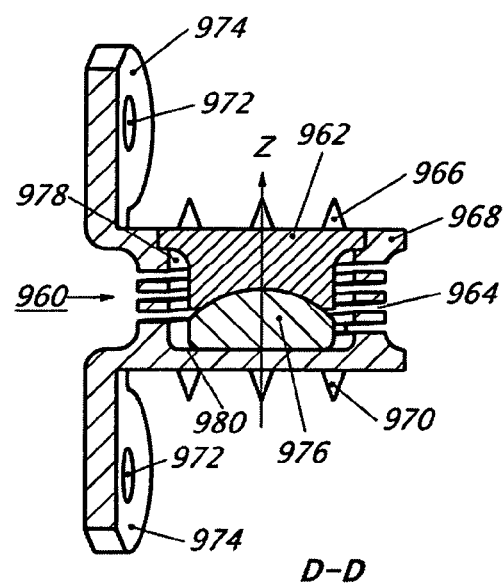
FIG. 23 shows a cross-sectional side view of the intervertebral disc prosthesis along line D-D as shown in FIG. 22.

Referring now to FIGS. 21-23, an intervertebral disc prosthesis 960 in another embodiment has a resilient member 968, a first support member 976 and a second support member 962. The resilient member 968 has a first end portion 904, a second end portion 906, and a body portion 908 defining a cavity 978 therebetween the first end portion 904 and the second end portion 906 with an axis Z. The body portion 908 has a helical slit 964 cut therein so as to allow the intervertebral disc prosthesis 960 to bend about three orthogonal axes including the axis Z. The helical slit 964 has at least one round formed around the body portion 908. The first end portion 904 includes a flanged edge 904a. The second end portion 906 includes a bottom portion 910 that substantially closes the cavity 978, where the bottom portion 910 has a flanged edge 910a, a first surface 912 and a second, opposite surface 914.

The first support member 976 has a curved surface and a substantially planar surface and is sized such that when the first support member 976 is housed within the cavity 978 of the resilient member 968 by cooperating with the substantially planar surface of the first support member 976 with the first surface 912 of the bottom portion 910 of the second end portion 906 of the resilient member 968, the first support member 976 is able to translate along two orthogonal axes that are perpendicular to the axis Z with respect to the first surface 912 of the bottom portion 910.

The second support member 962 has a curved surface and a substantially planar surface. The curved surface of the second support member 962 is substantially complementary to the curved surface of the first support member 976 so as to articulate the second support member 962 for allowing rotation about three orthogonal axes including the axis Z when the second support member 962 is received in the cavity the cavity 978 of the resilient member 968 by cooperating the curved surface of the second support member 962 with the curved surface of the first support member 976. In the embodiment of the intervertebral disc prosthesis 960, as shown in FIG. 23, the curved surface of the first support member 976 is a convex surface, while the curved surface of the second support member 962 is a concave surface that is substantially complementary to the convex surface. By receiving the second support member 962, the cavity 978 of the resilient member 968 is closed by the substantially planar surface of the second support member 962. The attachment of the second support member 962 to the resilient member 968 may be either rigid or in a way that the second support member 962 has the ability to rotate with respect to the resilient member 968.

As assembled, the intervertebral disc prosthesis 960 is a single piece construction that can generate a motion responsive to a possible movement of one or both of the first vertebra 200 and the second vertebra 202. The motion is a coupled motion among the resilient member 968, the first support member 976 and the second support member 962 and allows extension, flexion, axial rotation and lateral bending for a wearer of the intervertebral disc prosthesis 960.

To secure the intervertebral disc prosthesis 960 to the first vertebra 200 and the second vertebra 202, respectively, the first end portion 904 of the resilient member 968 has at least one engaging element protruding axially outwardly from the flanged edge 904a of the first end portion 904 to engage the first vertebra 200 in use, where the at least one engaging element has a plurality of teeth 966, as shown in FIGS. 21 and 22. Additionally, the first end portion 904 of the resilient member 968 has additional engaging means associated with the at least one engaging element to engage the first vertebra 200 in use, where the additional engaging means comprises a tab member 974 having at least one hole 972 for placement of a bone screw for additional attachment of the intervertebral disc prosthesis 960 to the first vertebra 200. The second end portion 906 of the resilient member 968 has at least one engaging element protruding axially outwardly from the flanged edge 906a of the second end portion 906 to engage the second vertebra 202 in use, where the at least one engaging element includes a plurality of teeth 976. Furthermore, the second end portion 906 of the resilient member 968 includes additional engaging means associated with the at least one engaging element to engage the second vertebra 202 in use, wherein the additional engaging means comprises a tab member 974 having at least one hole 972 for placement of a bone screw for additional attachment of the intervertebral disc prosthesis 960 to the second vertebra 202.

Figure 24:
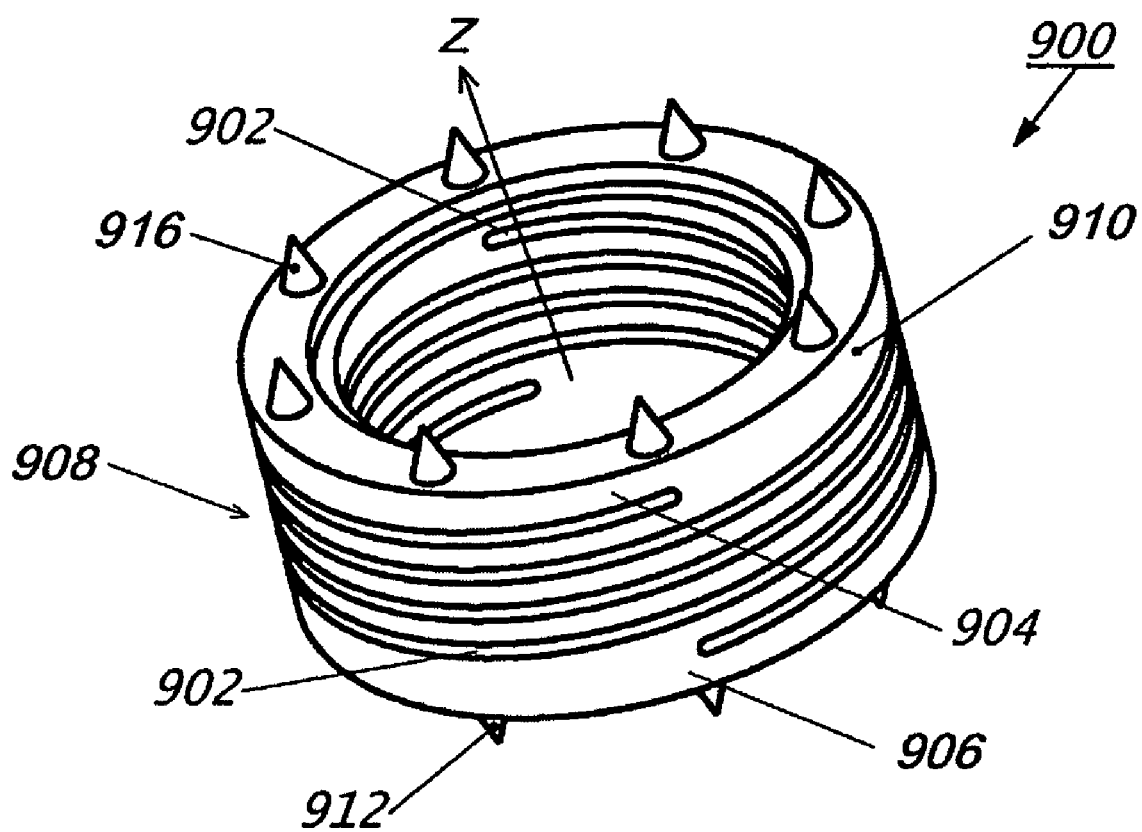
FIG. 24 shows a perspective view of an intervertebral disc prosthesis according to an alternative embodiment of the present invention.

Referring to FIG. 24, an intervertebral disc prosthesis 900 has a resilient member 910 having a first end portion 904, a second end portion 906, and a body portion 908 with an axis Z. The body portion 908 has a helical slit 902 cut therein so as to allow the intervertebral disc prosthesis 900 to bend about three orthogonal axes including the axis Z. The helical slit 902 has at least one round formed around the body portion 908. Alternatively, a plurality of helical slits may be cut into the body portion 908. The resilient member 910 can move in more than one possible direction responsive to a possible movement of at least one of the first vertebra 200 and the second vertebra 202.

In the embodiment of the intervertebral disc prosthesis 900, as shown in FIG. 24, the first end portion 904 of the resilient member 910 has at least one engaging element protruding axially outwardly from the first end portion 904 to engage the first vertebra 200 in use, where the at least one engaging element has a plurality of teeth 916. The second end portion 906 of the resilient member 910 has at least one engaging element protruding axially outwardly from the second end portion 906 to engage the second vertebra 202 in use, where the at least one engaging element includes a plurality of teeth 912.

In some embodiments, an intervertebral disc prosthesis of the present invention includes a resilient member, a first support member and a second support member that are made from same or different materials that are bio-compatible and surgically implantable. The bio-compatible and surgically implantable materials comprise at least one of ceramic, metal, composite, or polymer materials. The preferred material for the resilient member should possess high fatigue strength such as cobalt chrome alloy, titanium, titanium alloy, stainless steel, or the like. The material for the first support member and the second support member should possess excellent wear resistance and compressive strength. Ceramics, titanium, titanium alloy, stainless steel, cobalt chrome, composites, or polymers should preferably be used for these elements. Alternatively, a biocompatible material with a wear reducing coating could be used. For example, a wear reducing coating such as diamond-like coating may be used on the supports or the resilient member. In one embodiment, at least one of the resilient member, the first support member and the second support member has a coating that includes a diamond-like material.

An intervertebral disc prosthesis of the present invention may be inserted into the spine using standard medical procedures. For example, see, Benzel, *Spine Surgery: Techniques, Complication Avoidance, and Management,* 1999, particularly in Section 11, pages 142-192, the contents of which are incorporated herein by reference. Additionally, when inserting the intervertebral disc prostheses of the present invention, the intervertebral disc prosthesis may be inserted such that the first support member is superior to (from a top view) the second support member. In other words, the intervertebral disc prosthesis may be used in a way such that the second support member is on the bottom and the first support member is on top. In certain situations, the intervertebral disc prosthesis of the present invention may be used without the first support member, the second support member, or both of them.

While there has been shown several and alternate embodiments of the present invention, it is to be understood that certain changes can be made as would be known to one skilled in the art without departing from the underlying scope of the invention as is discussed and set forth above and below. Furthermore, the embodiments described above are only intended to illustrate the principles of the present invention and are not intended to limit the scope of the invention to the disclosed elements.

What is claimed is:

1. An intervertebral disc prosthesis for placement between a first vertebra and a second vertebra adjacent to the first vertebra, comprising:

a resilient member arranged, in use, to be secured to the first vertebra and the second vertebra, respectively, having a first end portion, a second end portion, and a body portion defining a cavity therebetween the first end portion and the second end portion, wherein the second end portion includes a substantially planar surface;

a first support member having a curved surface, a substantially planar surface and a body portion defined therebetween the curved surface and the substantially planar surface; and a second support member having a substantially planar surface, a curved surface and a body portion defined therebetween the substantially planar surface and the curved surface, wherein both of the first support member and the second support member are received in the cavity of the resilient member such that the substantially planar surface of the first support member cooperates with the substantially planar surface of the second end portion of the resilient member, and the curved surface of the second support member cooperates with the curved surface of the first support member, respectively, for generating a motion in more than one possible direction responsive to a possible movement of at least one of the first vertebra and the second vertebra.

2. The intervertebral disc prosthesis of claim 1, wherein the body portion has an axis, and a slit formed therein.

3. The intervertebral disc prosthesis of claim 2, wherein the slit has at least one round around the axis.

4. The intervertebral disc prosthesis of claim 3, wherein the slit is substantially in the form of at least one helical cut formed in the body portion.

5. The intervertebral disc prosthesis of claim 3, wherein the slit is substantially in the form of a double helical cut formed in the body portion.

6. The intervertebral disc prosthesis of claim 3, wherein the slit has an axis approximately coincident with the axis of the body portion.

7. The intervertebral disc prosthesis of claim 3, wherein the slit has a first end and a second end, each of the first end and the second end terminating in an opening.

8. The intervertebral disc prosthesis of claim 3, wherein the slit has a thickness that can be either substantially constant or variable along the slit.

9. The intervertebral disc prosthesis of claim 2, wherein the body portion has at least one more slit formed therein in addition to the slit.

10. The intervertebral disc prosthesis of claim 1, wherein the first end portion comprises a substantially circular edge portion.

11. The intervertebral disc prosthesis of claim 10, further comprising at least one engaging element protruding axially outwardly from the substantially circular edge portion to engage the first vertebra.

12. The intervertebral disc prosthesis of claim 11, wherein the at least one engaging element comprises a plurality of teeth.

13. The intervertebral disc prosthesis of claim 10, wherein the body portion of the second support member engages the substantially circular edge portion of the first end portion radially.

14. The intervertebral disc prosthesis of claim 13, wherein the substantially planar surface substantially closes the cavity substantially at the substantially circular edge portion.

15. The intervertebral disc prosthesis of claim 1, wherein the second end portion comprises a substantially circular edge portion.

16. The intervertebral disc prosthesis of claim 15, further comprising at least one engaging element protruding axially outwardly from the substantially circular edge portion to engage the second vertebra.

17. The intervertebral disc prosthesis of claim 16, wherein the at least one engaging element comprises a plurality of teeth.

18. The intervertebral disc prosthesis of claim 15, wherein the second end portion further comprises a bottom portion that engages the substantially circular edge portion of the second end portion radially.

19. The intervertebral disc prosthesis of claim 18, wherein the bottom portion is defined by a first substantially planar surface, and a second, opposite substantially planar surface.

20. The intervertebral disc prosthesis of claim 19, wherein the first substantially planar surface substantially closes the cavity substantially at the substantially circular edge portion.

21. The intervertebral disc prosthesis of claim 1, wherein in use the motion generated responsive to a possible movement of at least one of the first vertebra and the second vertebra possibly is a coupled motion among the resilient member, the first support member and the second support member and allows extension, flexion, axial rotation and lateral bending for a wearer of the intervertebral disc prosthesis by deformation of the intervertebral disc prosthesis.

22. The intervertebral disc prosthesis of claim 21, whereby the first support member and the second support member communicate to act as a transferor of force generated responsive to a possible movement of at least one of the first vertebra and the second vertebra.

23. The intervertebral disc prosthesis of claim 1, wherein the curved surface of the second support member and the curved surface of the first support member are substantially complimentary to each other.

24. The intervertebral disc prosthesis of claim 23, wherein one of the curved surface of the second support member and the curved surface of the first support member comprises a convex surface, and the other comprises a concave surface that is complimentary to the convex surface.

25. The intervertebral disc prosthesis of claim 1, wherein the resilient member, the first support member and the second support member are made from same or different materials that are bio-compatible and surgically implantable.

26. The intervertebral disc prosthesis of claim 25, wherein the bio-compatible and surgically implantable materials comprise at least one of ceramic, metal, composite, or polymer materials.

27. The intervertebral disc prosthesis of claim 1, wherein at least one of the resilient member, the first support member and the second support member has a wear reducing coating.

28. An intervertebral disc prosthesis for placement between a first vertebra and a second vertebra adjacent to the first vertebra, comprising:

a resilient member arranged, in use, to be secured to the first vertebra and the second vertebra, respectively, having a first end portion, a second end portion, and a body portion defining a cavity therebetween the first end portion and the second end portion with an axis Z, wherein the second end portion includes a bottom portion that substantially closes the cavity at the second end portion, the bottom portion having a first surface and a second, opposite surface;

a first support member having a first surface, a second surface and a body portion defined therebetween, wherein one of the first surface and a second surface comprises a curved surface, and the other comprise a substantially planar surface, wherein the first support member is received in the cavity of the resilient member such that the second surface of the first support member cooperates with the first surface of the bottom portion of the resilient member, for generating a motion in more than one possible direction responsive to a possible movement of at least one of the first vertebra and the second vertebra, wherein one of the first surface and the second surface of the first support member comprises a curved surface, and the other comprises a substantially planar surface, and wherein the second surface of the first support member cooperates with the first surface of the bottom portion of the resilient member to allow the support member to move axially along the axis Z, translate radially, rotate around the axis Z, and rotate around an axis that is different from the axis Z; and a second support member having a first surface, a second surface and a body portion defined therebetween, wherein one of the first surface and the second surface of the second support member comprises a curved surface, and the other comprises a substantially planar surface, and wherein the second support member is received in the cavity of the resilient member such that the second surface of the second support member cooperates with the first surface of the first support member, for generating a motion in more than one possible direction responsive to a possible movement of at least one of the first vertebra and the second vertebra.

29. The intervertebral disc prosthesis of claim 28, wherein the resilient member comprises a bellows member.

30. The intervertebral disc prosthesis of claim 28, wherein the second surface of the first support member cooperates with the first surface of the bottom portion of the resilient member to allow the support member to move axially along the axis Z, translate radially, rotate around the axis Z, and rotate around an axis that is different from the axis Z.

31. The intervertebral disc prosthesis of claim 28, wherein the second surface of the second support member and the first surface of the first support member are substantially complimentary to each other.

32. The intervertebral disc prosthesis of claim 31, wherein one of the second surface of the second support member and the first surface of the first support member comprises a convex surface, and the other comprises a concave surface that is complimentary to the convex surface.

33. The intervertebral disc prosthesis of claim 32, wherein the first surface of the second support member substantially closes the cavity at the first end portion.

34. An intervertebral disc prosthesis for placement between a first vertebra and a second vertebra adjacent to the first vertebra, comprising:

a resilient member arranged, in use, to be secured to the first vertebra and the second vertebra, respectively, having a first end portion, a second end portion, and a body portion defining a cavity therebetween the first end portion and the second end portion with an axis Z, wherein the second end portion includes a bottom portion that substantially closes the cavity at the second end portion, wherein the resilient member can move in more than one possible direction responsive to a possible movement of at least one of the first vertebra and the second vertebra, and wherein the bottom portion has a first surface and a second, opposite surface;

a first support member having a first surface, a second surface and a body portion defined therebetween, wherein one of the first surface and a second surface comprises a curved surface, and the other comprise a substantially planar surface, and wherein the first support member is received in the cavity of the resilient member such that the second surface of the first support member cooperates with the first surface of the bottom portion of the resilient member, for generating a motion in more than one possible direction responsive to a possible movement of at least one of the first vertebra and the second vertebra; and a second support member having a first surface, a second surface and a body portion defined therebetween, wherein one of the first surface and a second surface comprises a curved surface, and the other comprise a substantially planar surface, and wherein the second support member is received in the cavity of the resilient member such that the second surface of the second support member cooperates with the first surface of the first support member, for generating a motion in more than one possible direction responsive to a possible movement of at least one of the first vertebra and the second vertebra.

35. The intervertebral disc prosthesis of claim 34, wherein the resilient member comprises a bellows member.

36. The intervertebral disc prosthesis of claim 35, wherein the bellows member permits possible motions related to the axis Z and at least one additional axis that is perpendicular to the axis Z.

37. The intervertebral disc prosthesis of claim 36, wherein the bellows member permits possible motions related to a third axis that is perpendicular to the axis Z and the at least one additional axis that is perpendicular to the axis Z.

38. The intervertebral disc prosthesis of claim 37, wherein the possible motions include extension, flexion, axial rotation and lateral bending.

39. The intervertebral disc prosthesis of claim 34, wherein the second surface of the second support member and the first surface of the first support member are substantially complimentary to each other.

40. The intervertebral disc prosthesis of claim 38, wherein one of the second surface of the second support member and the first surface of the first support member comprises a convex surface, and the other comprises a concave surface that is complimentary to the convex surface.

41. The intervertebral disc prosthesis of claim 40, wherein the first surface of the second support member substantially closes the cavity at the first end portion.

42. The intervertebral disc prosthesis of claim 39, wherein in use the motion generated responsive to a possible movement of at least one of the first vertebra and the second vertebra possibly is a coupled motion among the resilient member, the first support member and the second support member and allows at least extension, flexion, axial rotation and lateral bending for a wearer of the intervertebral disc prosthesis.

43. The intervertebral disc prosthesis of claim 39, wherein the resilient member, the first support member and the second support member are made from same or different materials that are bio-compatible and surgically implantable.

* * * * *